United States Patent [19]

Faust et al.

[11] 4,090,374
[45] May 23, 1978

[54] APPARATUS FOR CRYOGENIC FREEZING OF FLUID FILLED POUCHES

[75] Inventors: Clifford C. Faust, Riverside; Philip F. Cilia, Bridgeview, both of Ill.

[73] Assignee: Union Carbide Corporation, New York, N.Y.

[21] Appl. No.: 831,425

[22] Filed: Sep. 8, 1977

Related U.S. Application Data

[60] Continuation of Ser. No. 580,170, May 23, 1975, abandoned, which is a division of Ser. No. 176,214, Aug. 30, 1971, Pat. No. 3,952,536.

[51] Int. Cl.$^2$ ............................................. F25C 5/14
[52] U.S. Cl. ....................................... 62/341; 206/451
[58] Field of Search ........................... 62/60, 341; 206/403–406, 449, 450, 451, 472–474

[56] References Cited

U.S. PATENT DOCUMENTS

| | | | |
|---|---|---|---|
| 2,260,450 | 10/1941 | Guinane | 62/60 |
| 2,964,920 | 12/1960 | Staebler | 62/60 |
| 2,968,568 | 1/1961 | Preuss | 62/63 |
| 3,452,469 | 7/1969 | White | 43/55 |
| 3,576,650 | 4/1971 | Underwood et al. | 62/64 |
| 3,612,233 | 10/1971 | Nagpal et al. | 206/403 |
| 3,683,635 | 8/1972 | Campanelli | 62/64 |

OTHER PUBLICATIONS

*Modern Problems of Blood Preservation* (Spielman et al., eds.), Stuttgard, G. F. Verlag, 1970, pp. 168–175: "Low Temperature Preservation of Red Cells Using Fast Freezing Method & Low Glycerol in Plastic Containers": Pert et al.
*Modern Problems of Blood Preservation* (Spielman et al., eds.), Stuttgard, G. F. Verlag, 1970, pp. 157–160: "A Plastic Bag System for Freezing, Thawing & Washing of Red Cells": Akerblom et al.
*Proceedings 10th Congress International Society Blood Transfusion*, Stockholm, 1964, pp. 674–682, (1965), "Low Temperature Preservation of Human Erythrocytes": Pert et al.

*Primary Examiner*—Ronald C. Capossela
*Attorney, Agent, or Firm*—Alvin H. Fritschler

[57] ABSTRACT

Viable fluids such as blood components are rapidly frozen in plastic or the like pouches for transportation and/or storage by placing a flat pouch slack filled with fluid between two substantially planar parallel restraining surfaces such as metal plates of greater perimeter than the flattened slack filled pouch which are rigid enough to prevent sagging of the pouch when it is vertically disposed and flexible enough to accommodate expansion of the pouch flat sides during the freezing operation. The restraining surfaces are retained against separation by retaining means applied against at least a portion of the outer surfaces of each pouch restraining means and the entire assembly is immersed in a cryogenic medium to rapidly freeze the fluid.

7 Claims, 7 Drawing Figures

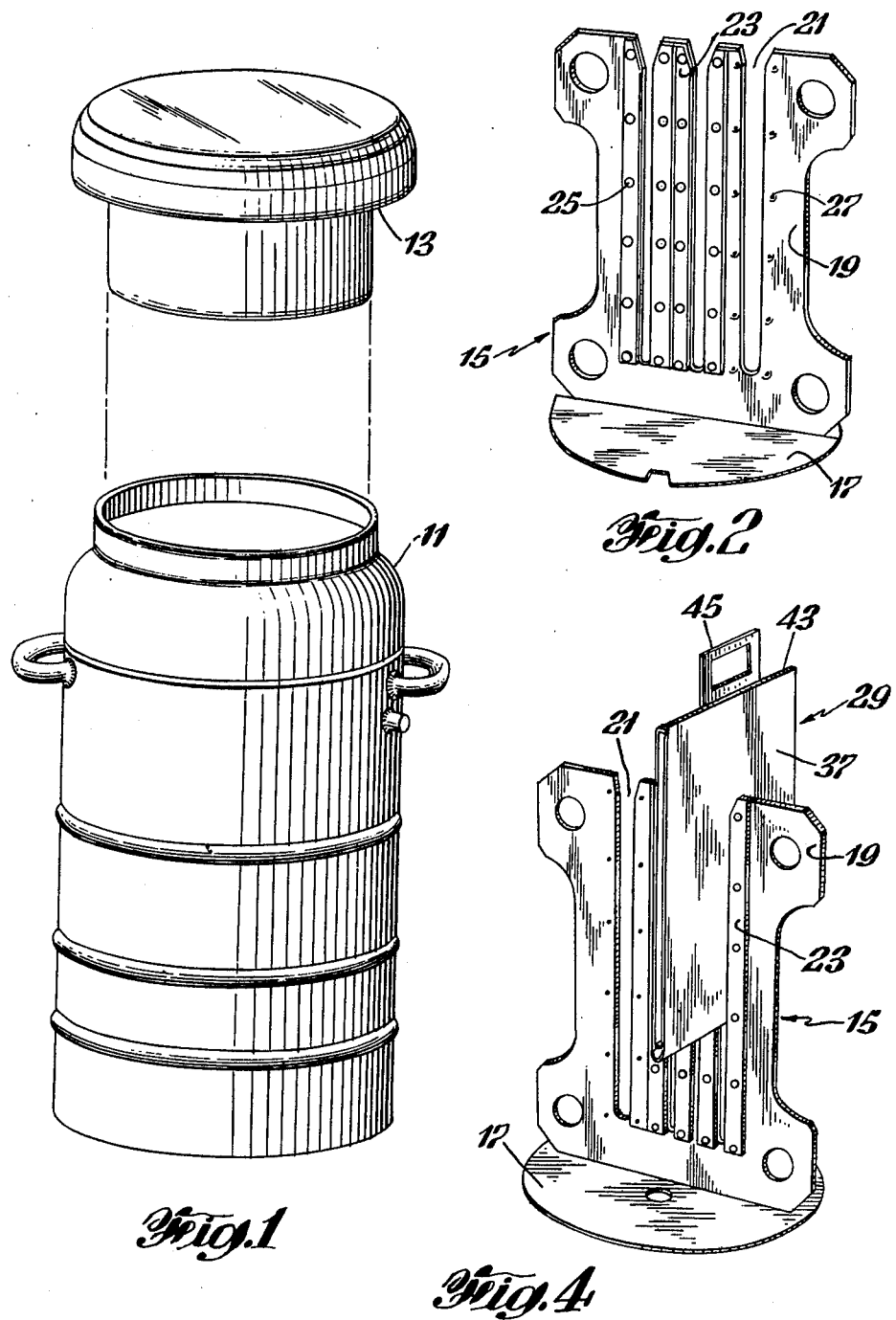

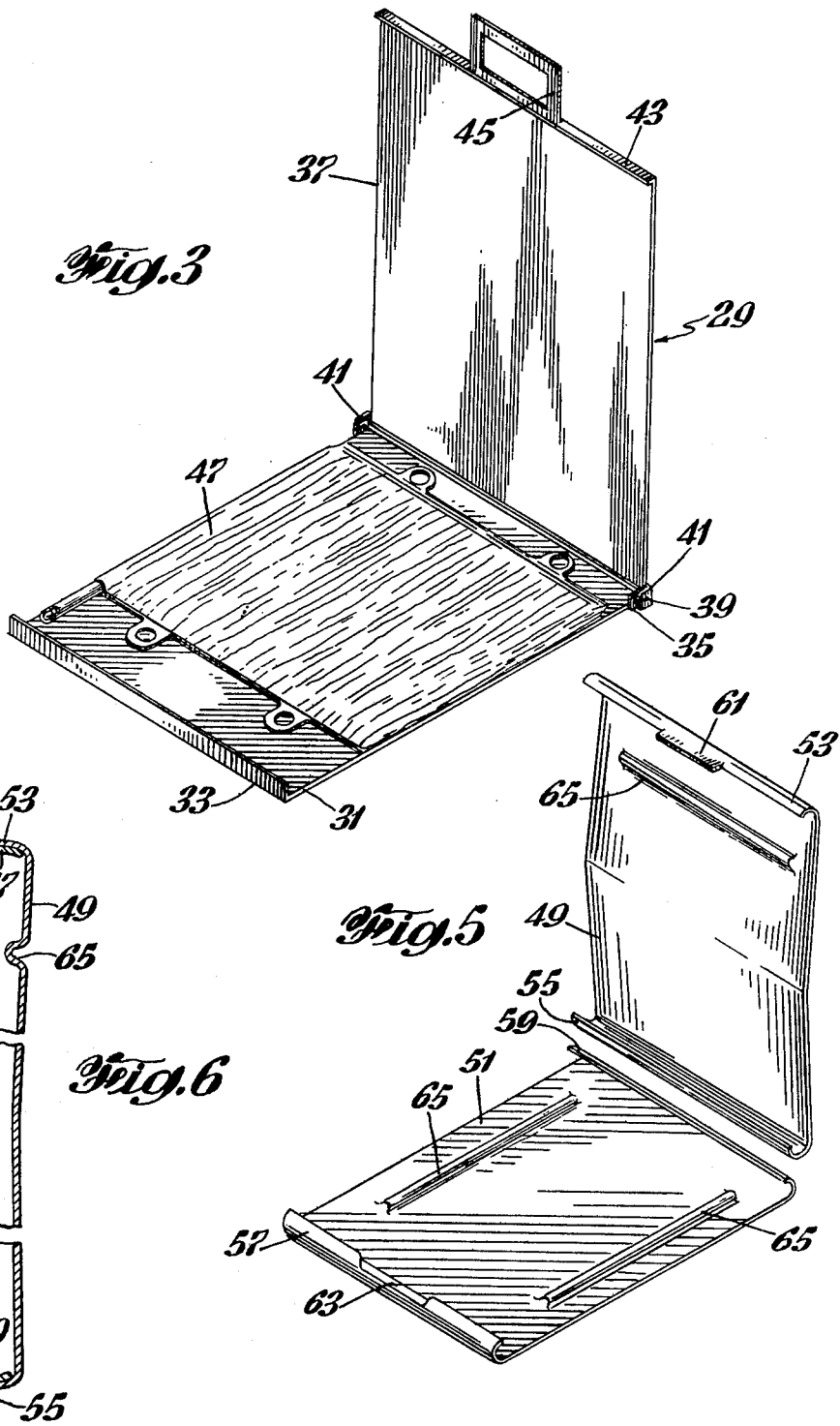

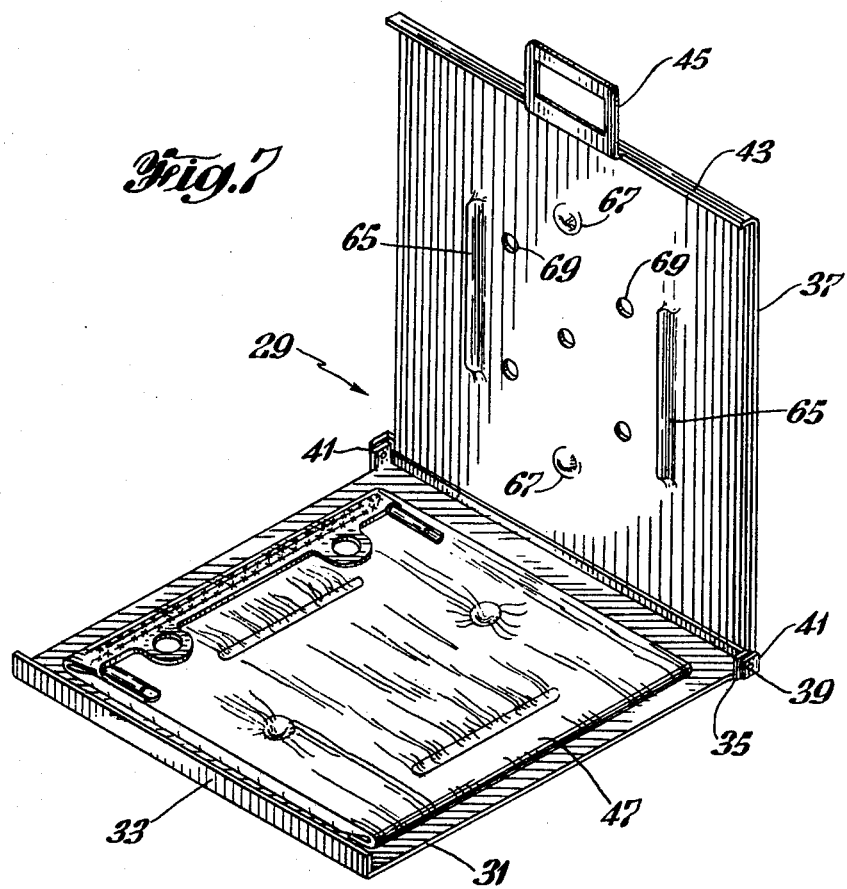

APPARATUS FOR CRYOGENIC FREEZING OF FLUID FILLED POUCHES

CROSS REFERENCE TO RELATED APPLICATIONS

This application is a Continuation of Ser. No. 580,170 filed May 23, 1975 now abandoned which in turn is a Divisional of Ser. No. 176,214 filed Aug. 30, 1971 now U.S. Pat. No. 3,952,536.

This invention relates to a method and apparatus for rapid freezing fluids into uniformly thin layer like transportable and storable unitary packages handled at cryogenic temperatures in the order of about that of liquid nitrogen. More particularly, the present invention relates to a method and apparatus for the packaging and rapid freezing of viable and perishable fluids, particularly biomedical fluids such as blood, blood platelets and other fluid components of blood into thin layer like package units which are easily handled and stored at cryogenic temperatures without suffering breakage, leakage, contamination or other damage.

The effective and efficient sterile packaging and preservation for future use of biological fluids such as fluid components of blood has long been and continues to be of great importance and interest in the biomedical arts. Significant progress has been made in this area using rapid freeze preservation techniques involving a variety of cryoprotective systems in conjunction with freeze-thaw-wash methods applied to such fluids in containers. Preservatives and/or cryoprotective agents such as glycerol and other additives may also be included in the containers with the fluid to be processed in quantities and manners within the ken of persons familiar with the art. This new technology makes possible hitherto unattainable desiderata such as the ready availability from freeze storage of blood platelets for leukemia patient treatments, rare blood type components which may now be effectively preserved and stored, red blood cells for treatment of oxygen deficiency cases and the facile handling of blood plasma. With regard to freezing operations on such fluids, the cellular components of blood in particular, it is important to maintain the fluid mass in as uniform a cross section as possible mainly in order to attain the controllable rapid freeze and thaw rates essential to the prevention of rupture or other damage to the cells and also to produce a uniform product suitable for storage. It has been found that a relatively uniform flat thin cross section is particularly suitable and yields a high quality product with nicely controllable rapid freeze and thaw rates. These desirable relatively flat thin and uniform cross sections are obtained inherently with the use of flexible flat packages or pouches such as the pouches described and illustrated in U.S. Pat. No. 3,576,650 to Underwood. A flexible pouch has a maximum fluid containing capability equal to the volume of the spherical form it will naturally assume when filled while unrestrained in any manner. Since the fluid containing volume of such a pouch however lessens considerably as the pouch shape changes from the spherical to the flat shape, it is necessary that the pouches in practicing this invention be slack filled, that is to say with a fluid volume not more than will insure maintenance of the desired thickness and shape when held flattened and restrained. In order to maintain this desired cross section and overall package configuration with such pouches during the freezing operation they must perforce be kept flattened and an obvious way to do this is to freeze the fluid filled packages in a horizontal orientation. The freezing of horizontally oriented flat packaged fluids however has been found adversely to affect the rapidity and uniformity of freeze rates because when a fluid filled package and its support are immersed in the cryogenic medium, liquid nitrogen for instance, gas bubbles of the vaporized freezing medium form beneath the underside of the horizontally disposed assembly creating random insulative pockets which interfere with an even and rapid heat transfer from the product being frozen.

Efforts to obviate the problems attending rapid horizontal freezing of such fluids have led to the development and use of thin rigid stainless steel fluid containers which maintain the fluid cross section as desired independently of container position, can be immersed vertically in the freezing medium and make for very rapid freeze rates due to the good thermal conductivity of the metal. Such containers are also suitably durable and puncture resistant for handling, transport and storage. There are however numerous disadvantages to these metal containers. First and of great importance the necessity of venting a viable fluid metal container to the atmosphere during both filling and dispensing makes for difficulty in maintaining the sterility essential to the use of such product particularly in effecting a sterile closure on the filled container. Since the metal is opaque it is impossible to inspect the inside of the container for the possible presence of particulate foreign matter or other visible indicia of contamination or to see the contained product itself. The container units are expensive to fabricate and are not reusable. Further, it is virtually impossible to apply any sort of kneading action when desired to effect mixing of the fluid product during the thaw process since the container metal walls cannot be kneaded in the manner of flexible plastic pouches.

Thus it can be seen that efforts to date in the art of cryogenic processing of viable and perishable fluids have solved one set of problems only to encounter others. Further efforts directed to improving either the horizontal or the vertical freezing techniques similarly have produced less than completely satisfactory results.

So was the state of the art at the time the present invention was conceived and developed with the object of providing a method and apparatus for the rapid vertical freezing of viable and perishable fluids in plastic pouches while attaining the benefits but none of the disadvantages attaching to the use of the metal containers heretofore used in vertical freezing techniques.

It is a further and important object of this invention to provide a method and apparatus for the cryogenic freezing of viable and perishable fluids, particularly fluid blood components, which is uncomplicated, easily used and maintained sterile and which produces a product which can be handled, transported, stored and utilized without the need for any extraordinary protection against physical damage.

A still further object of the invention is to provide a packaged blood component freezing method and apparatus which are capable of making the desired packaged frozen blood product inexpensively using commercially available plastic sterile pouches which are readily discardable after a single utilization with minimal waste material accrual.

These and other objects of the present invention will be the more readily understood from the ensuing description and the drawings wherein FIG. 1 is a perspective view of a cryogenic media container and its cover.

FIG. 2 is a perspective view of a jig fixture for retaining plate restrained bagged fluids in a container during freezing.

FIG. 3 is a perspective view of a hinged closeable restraining plate set used in conjunction with the jig of FIG. 2 showing a fluid filled pouch in place on one of the plates.

FIG. 4 is a perspective view of the jig fixture of FIG. 2 with a loaded restraining plate set of FIG. 3 partly inserted.

FIG. 5 is a perspective view of an alternative form of plate set for restraining bagged fluids.

FIG. 6 is an enlarged fragmented cross section through the assembled plate set of FIG. 5 and FIG. 7 is a perspective view of a modified form of hinged plate set.

In general the present invention comprehends freezing fluids into thin layer-like transportable and storable unitary packages comprising, in combination, slack filling a pouch of flexible plastic material with a fluid to be frozen, flattening and disposing the slack filled pouch between two closely spaced substantially parallel planar surfaces, restraining the surfaces against separation from the flattened pouch disposed therebetween with a retaining force sufficient to prevent sagging distortion of the unfrozen fluid filled package when it is vertically disposed applied to a portion of said surfaces less than the total surface area, immersing the assembled fluid filled package and the retained restraining surfaces in a substantially vertical orientation into a cryogenic medium having a temperature on the order of about that of liquid nitrogen for a time sufficient to effect solid freezing and continued subcooling of the packaged fluid down to the preselected cryogenic temperature.

With reference to the drawings, FIG. 1 shows a cryogenic medium container and its cover, specifically a liquid nitrogen container 11 and cover 13 used in the freezing operations according to the invention. Liquid nitrogen at a temperature in the order of about $-196°$ C. fills container 11 and fast freezes the fluids immersed therein within a matter of seconds. A jig shown generally at 15 in FIG. 2 is used interiorly of container 11 to support the plate restrained slack filled pouches or bags being frozen. Jig 15 comprises a circular flat base 17 to which is perpendicularly centrally attached an upright plate retainer 19 cut or cast from flat stock to define slots 21 disposed to hold the bags and restraining plates. Insulating strips 23 of any suitable preferably nonmetallic material may also be provided and attached to the plate retainer 19 by means of screws 25 in holes 27 or any other suitable attachment means. Insulating strips 23 are provided mainly to effect friction reduction in sliding the assembled plates into and out of the jig fixture and to prevent galling or seizing of the jig metal to plate metal contacts which is known to occur at cryogenic temperatures. The insulating strips 23 also obviate heat flow losses between the plates pouch assembly and the jig fixture metal mass but this consideration is not of great significance when the jig fixture assembly is left normally to reside in the cryogenic medium container.

FIG. 3 shows a restraining plate set indicated generally as 29 used in conjunction with the jig of FIG. 2. The restraining plate set 29 comprises a first plate 31 having a closure return 33 along one edge and hinge bosses 35 at the opposite end. Plate 31 is hinge connected to a second plate 37 with hinge pins 39 fitted through the first plate hinge bosses 35 and companion hinge bosses 41 on second plate 37. Second plate 37 is provided with a closure return 43 along the closure or edge opposite the hinged edge and with a handle 45. Other than the closure returns 33, 43, the hinge bosses 35, 41 and, if desired, additional edge returns along the hinged side, the plates have no other edge returns. It is of significance in the present invention to provide return-free edges along the sides other than the closure side and hinge side to obviate plate buckling and other undesirable distortion which have been found to occur with the use of plates having full perimeter returns. A transparent plastic pouch 47 slack filled with fluid and flattened is shown arranged on the first plate 31.

In using the above described apparatus according to the present invention, a pouch 47 is slack filled with the fluid to be frozen, laid flat on the first or lower plate of hinged restraining plate set 29, the plate set is closed and the assembly slid vertically into a slot 21 of the jig 15 as illustrated in FIG. 4 of the drawings. The lines of contact are along the vertical centers of the outer surfaces of the plates 31, 37 and the friction reducing insulating strips 23 as shown and, in instances where for one reason or another the jig fixture is being loaded outside the cryogenic medium container, there is little or no contact of high heat conduction significance between the plate set 29 and fluid to be frozen and the mass of plate retainer 19. One or more slack filled pouches and restraining plate sets may be loaded into the jig fixture 15 depending upon the respective sizes and shapes of the cryogenic medium container, the flat fluid filled pouches in vertical orientation in their respective restraining plate sets and, to some minor extent, the desired freezing rate. The loaded jig fixture is lowered into the liquid nitrogen container 11, which may then be closed with cover 13, for a time sufficient to effect the freezing of the fluid, the cover if used is removed, the loaded jig lifted out and unloaded and the product, comprising the frozen fluid filled pouch and its set of restraining plates, now acting as physical protectors for the pouch, is ready as a package for storage, shipment and so forth under low temperature cryogenic environments. In usual practice according to the invention however, the unloaded jig 15 fixture assembly is left to reside permanently within the container 13 submerged in liquid nitrogen and the slack filled pouch 47 secured in the plate set is directed into the container and slid into a slot 21 of the jig in situ. Since there is little or no heat flow downward into an open container of liquid nitrogen such as would detrimentally affect the rapid freezing step, it is usually unnecessary to close the container 11 with its cover 13. During the freezing operation any expansion, which may be considerable, occurring cross sectionally in the fluid is easily accommodated since the retaining force on restraining plates 31, 37 is applied only vertically centrally of the assembly along the lines of contact with the insulating strips 23.

FIGS. 5 and 6 of the drawings show an alternative form of restraining plate set comprising two separate plates 49 and 51 which clip together without hinge means and thus restrain the fluid filled bag to be frozen. Plate 49 is provided with curved edge returns 53 and 55 which snap over companion edge returns 57, 59 provided on plate 51. To insure alignment of the assembled plates 49, 51 and to facilitate opening, a lip type protrusion 61 may be provided on one of the plates, 49 for example, to latch into a receptor slot 63 on the other plate. Alternatively but similarly the plates may be kept aligned and latched against lateral movement by means of a spring loaded pin or detent latch on one of the plates disposed to engage a hole or latch port on the other.

It has also been found advantageous to interrupt the flat planar surfaces of the bag contacting surfaces of restraining plates of all types with ridges 65 or dimples 67 or the like to lock or immobilize the slack filled bag in place for handling prior to freezing and to impart additional structural integrity to the frozen product after freezing. Further in this respect, one or the other or both plates of a set may be made foraminous by inclusion of perforations 69 therethrough illustrated in FIG. 7 of the drawings. It is important in the use of foraminous plates however that the holes not be overly large or sharp edged to avoid bag blistering and blister rim cutting occasioned by rapid freeze expansion. Foraminous plates provide the added advantage of prompting faster rapid freeze rates since the cryogenic freezing medium is in direct contact with exposed portions of the fluid filled pouch.

A further modification, and one which permits the elimination of the jig fixture 15 assembly if so desired, is to form one or the other or both of the restraining plates to a slightly concave shape as illustrated by the shape of plate 49 in FIGS. 5 and 6 of the drawings. Concave shaped plates yield to the expansive forces developed in the fluids being frozen and tend to produce a substantially uniform cross section flat planar parallel surfaced product at the completion of the freezing step. In the use of concave plates according to the present invention it is the concavity itself which imparts and applies the retaining force in part centrally to the restrained surfaces and, in the illustrated embodiment, applies such force centrally horizontally across the width of the slack filled pouch being frozen. Concave formed plates may also be employed successfully in the apparatus embodiment illustrated in FIG. 3 of the drawings and this embodiment may then also be utilized in the cryogenic medium container without the need for additional equipment such as the jig 15 fixture. Conversely, the unhinged embodiments of restraining plates such as illustrated in FIGS. 5 and 6 of the drawings may be used in conjunction with the jig 15 fixture either with or without the concavity feature depending on the choice of the practitioner.

In respect of planar interruptions such as exemplified by the ridges 65 and the dimples 67, other forms have been used successfully such as for example a full area grid form protrusion which imparts a waffle like appearance to the frozen fluid filled pouch.

While it has been expedient and inexpensive in most cases in practicing the present invention to transport, store and otherwise handle the frozen fluid product in the restraining plates, whatever type used, until utilization of the fluid, the restraining plate assemblies may be removed and the frozen fluid filled pouch used as the product. However, maximum protection for the frozen pouch is obtained by leaving the restraining plates on the pouch until the same time of utilization.

In the description of the present invention the term "substantially" in respect of the flatness, uniformity of cross section, planarity and parallelism of the restraining surfaces and plates is intended to so qualify these features as to include surface protrusions, intrusions, interruptions, and perforations, those described as well as others, the concavity of the plates in particular embodiments of apparatus according to the invention and the bowing or other slight deformation of the plates occurring inherently due to freeze expansion of the pouch cross section. Similarly, the term "separable" as applied to the plates according to the invention is intended to mean that the plates may be connected by hinges or similar means, the only essential requirement being that they are capable of being opened to receive a fluid filled package and closable over it.

The mechanical components of the present invention may be made of any materials capable of low temperature duty. Aluminum has been found particularly suitable for the restraining plates and the jig fixture. Stainless steel has also been used. Any durable plastic capable of withstanding low temperatures is suitable for the insulating strips 23. A bag or pouch type which has been used successfully in practicing the invention is made of seamless oriented polyolefin tubing having a wall thickness of 0.075mm, flattened, cut and heat sealed at the open edges to make a flat length of approximately 27cm and a flat width of approximately 28cm. It is customary in such pouches to have a second heat seal parallel to the first at the top of the pouch to insure firm anchoring of the vent and filling-dispensing tubes attached to the pouch. When filled without the application of restraint of any kind, that is to say while freely suspended, the fluid capacity of such a pouch is about 4,000ml. In actual use the bag is slack filled to about from 550ml to 600ml, usually depending on the volume of the donor specimen. With this order of slack filled volume the flattened bag will enclose a fluid thickness of from 5mm to 10mm, a preferred fluid thickness being from about 7mm to about 8mm.

EXAMPLES

Several laboratory tests were performed freezing human whole blood according to the present invention. In these tests samples were prepared using bags similar to those described hereinabove each having a tubing wall thickness of 0.075mm, a heat seal at the bottom, two parallel heat seals at the top, a length between seals of approximately 26.5cm and a flat width of about 28.0cm. The bags were slack filled each to about 575ml with blood, and placed flattened to a thickness of about 7.5mm into restraining plate sets of the type shown in the drawings.

The restraining plate sets employed were made of aluminum sheets of 0.157mm thickness, about 28cm width and about 30cm length. One plate of each set was provided two longitudinally extending protrusions or retention ribs each about 10cm long and the other plate with a laterally extending retention rib about 12.5cm long. These ribs were about 0.8cm wide and protruded inwardly to the contained pouch from about 2mm to about 3mm from the plate inner surface.

The prepared samples were frozen in about 30 seconds in liquid nitrogen, subcooled for about 5 minutes, some with a jig 15 fixture and some without, removed from the liquid nitrogen and the restraining plates left on.

These frozen product samples were handled, stored and ultimately thawed with ease and with complete maintenance structural and sterile integrity. Several such samples were drop tested in end and corner drops from a height of about 2 feet to a concrete floor and suffered no pouch rupture.

In respect of structural integrity, protection against drop damage in particular, it is advantageous to load the slack filled pouches transversely into the restraining plates, that is with the heat seals at right angles to the restraining plate set closure returns, parallel to the plate set open edges and with the heat seals folded over or under the flattened pouch prior to plate set closure and freezing. This technique which is illustrated in FIG. 7 of the drawings will more effectively insulate the heat seals and their junctures with the pouch main body, areas which are somewhat weaker than the overall body of the pouch, from shock damage such as occasioned by accidental drops.

In the light of the foregoing disclosure numerous alternative modes of practicing the present invention, but within its scope and spirit, will undoubtedly occur to persons familiar with the art. It is intended therefore that the specification and appended drawings be considered illustrative only and not construed in any limiting sense.

What is claimed is:

1. Apparatus for cryogenically freezing fluids in a flexible, slack filled pouch into a thin, layer-like package article comprising:
a restraining plate set with two substantially flat parallel planar plates capable of thermal conductivity at cryogenic temperatures, said plates being separable to permit enclosure therebetween of said slack filled pouch to be frozen, each of said plates having edge closure returns on one side thereof and return-free edges along the sides other than said edge closure return side, the interior surface planarity of at least one of said plates having a protrusion extending into less than completely through the space between said plates when they are disposed in their parallel planar orientation.

2. Apparatus as defined in claim 1 wherein said plates are selectably closeable by hinge means connecting respective plate corresponding edges.

3. Apparatus as defined in claim 2 further including edge returns along the hinged side of each of said plates.

4. Apparatus as defined in claim 1 wherein the protrusion extending into less than completely through the space between the plates is a convexity pressed from the plate surface.

5. Apparatus as defined in claim 4 wherein said convexity is a generally circular convexity.

6. Apparatus as defined in claim 1 wherein the protrusion extending into less then completely through the space between the plates is an elongate rod element attached to a plate interior surface.

7. Apparatus as defined in claim 1 further including edge returns along the side of each of said plates opposite said edge closure return side.

* * * * *